(12) United States Patent
Luo et al.

(10) Patent No.: US 9,653,497 B2
(45) Date of Patent: May 16, 2017

(54) MANUFACTURING METHOD OF SENSING INTEGRATED CIRCUIT

(71) Applicant: TAIWAN SEMICONDUCTOR MANUFACTURING CO., LTD., Hsinchu (TW)

(72) Inventors: Tzo-Hung Luo, Taichung (TW); Chin-Hung Chiang, Hsinchu (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 0 days.

(21) Appl. No.: 14/849,380

(22) Filed: Sep. 9, 2015

(65) Prior Publication Data

US 2015/0380446 A1      Dec. 31, 2015

Related U.S. Application Data

(62) Division of application No. 14/156,860, filed on Jan. 16, 2014, now Pat. No. 9,171,873.

(51) Int. Cl.
| | | |
|---|---|---|
| *H01L 27/144* | (2006.01) | |
| *H01L 21/768* | (2006.01) | |
| *H01L 31/18* | (2006.01) | |
| *H01L 31/0224* | (2006.01) | |
| *H01L 31/032* | (2006.01) | |
| *H01L 31/09* | (2006.01) | |
| *H01L 51/42* | (2006.01) | |
| *H01L 51/44* | (2006.01) | |
| *H01L 21/8234* | (2006.01) | |
| *H01L 31/0272* | (2006.01) | |
| *H01L 31/0232* | (2014.01) | |
| *H01L 31/0216* | (2014.01) | |
| *H01L 31/02* | (2006.01) | |

(Continued)

(52) U.S. Cl.
CPC .... *H01L 27/1446* (2013.01); *H01L 21/02057* (2013.01); *H01L 21/02568* (2013.01); *H01L 21/8234* (2013.01); *H01L 27/1443* (2013.01); *H01L 31/02005* (2013.01); *H01L 31/0224* (2013.01); *H01L 31/0272* (2013.01); *H01L 31/02161* (2013.01); *H01L 31/02327* (2013.01); *H01L 31/0324* (2013.01); *H01L 31/09* (2013.01); *H01L 31/18* (2013.01); *H01L 51/42* (2013.01); *H01L 51/441* (2013.01); *H01L 51/0042* (2013.01); *H01L 2031/0344* (2013.01)

(58) Field of Classification Search
CPC ..... H01L 27/144; H01L 21/768; H01L 31/18; H01L 51/42; H01L 51/44
USPC .......... 250/214.1, 208.1, 338.4, 332, 339.02; 257/759
See application file for complete search history.

(56) References Cited

U.S. PATENT DOCUMENTS 5,900,630 A      5/1999   Tang et al.
6,288,388 B1 *   9/2001   Zhang et al. .............. 250/214.1
(Continued)

*Primary Examiner* — Sheng Zhu
(74) *Attorney, Agent, or Firm* — Maschoff Brennan

(57) ABSTRACT

A manufacturing method of a sensing integrated circuit including the following acts. A plurality of transistors are formed. At least one dielectric layer is formed on or above the transistors. A plurality of connecting structures are formed in the dielectric layer. The connecting structures are respectively and electrically connected to the transistors. A plurality of separated conductive wells are respectively formed in electrical contact with the connecting structures.

20 Claims, 4 Drawing Sheets

(51) Int. Cl.
*H01L 21/02* (2006.01)
*H01L 51/00* (2006.01)
*H01L 31/0256* (2006.01)

(56) References Cited

U.S. PATENT DOCUMENTS

| | | |
|---|---|---|
| 6,864,950 B2 * | 3/2005 | Zhang et al. ................. 349/199 |
| 2008/0283954 A1 * | 11/2008 | Shim ............................. 257/443 |
| 2009/0014056 A1 | 1/2009 | Hockaday |
| 2009/0127435 A1 * | 5/2009 | Mochizuki et al. ....... 250/208.1 |

* cited by examiner

MANUFACTURING METHOD OF SENSING INTEGRATED CIRCUIT

PRIORITY CLAIM AND CROSS-REFERENCE

The present application is a divisional of U.S. application Ser. No. 14/156,860, filed on Jan. 16, 2014, the disclosure of which are hereby incorporated by reference herein in its entirely.

BACKGROUND

A sensor is a converter used to measure a physical quantity and then convert it into a signal. This signal may be read by an observer or by an electronic instrument. For example, a photodiode may convert the measured light input into a proportional current output, and a deoxyribonucleic acid (DNA) sensor may convert the measured energy of hydrogen bonds into an output voltage. The sensitivity of the sensor represents how much of the output when measuring the physical quantity, and a sensor with higher sensitivity can sense more tiny amount of the physical quantity.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
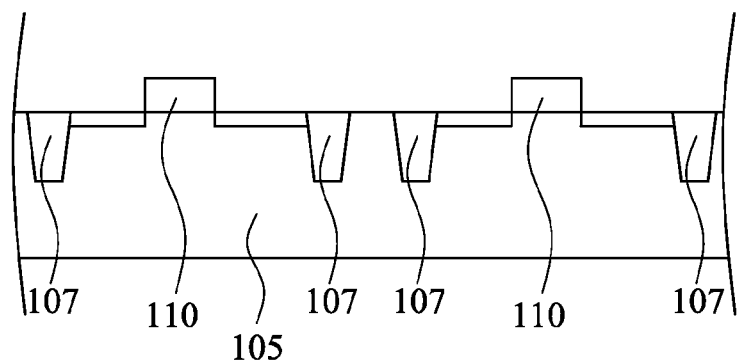
FIG. 1 to FIG. 7 are cross-sectional views of a method for manufacturing a sensing integrated circuit according to various embodiments of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

As used herein, the terms "comprising," "including," "having," "containing," "involving," and the like are to be understood to be open-ended, i.e., to mean including but not limited to.

In the digital world, integrated circuit (IC) technology continues to shrink in size. The pure digital technologies focus on the digital density and low cost. However, for a sensor with higher digital density and low cost, the sensitivity may be reduced, or crosstalk between adjacent two sensing units of the sensor may occur. Therefore, a light sensing integrated circuit and a method of a sensing integrated circuit can be provided.

FIG. 1 to FIG. 7 are cross-sectional views of a method for manufacturing a sensing integrated circuit according to various embodiments of the present disclosure. Reference is made to FIG. 1. A manufacturer may form a plurality of transistors 110. In greater detail, the manufacturer may form the transistors 110 on a substrate 105. To separate the transistors 110 from each other, a plurality of insulating portions 107 may be embedded in the substrate 105 and disposed between adjacent two of the transistors 110. In some embodiments, the substrate 105 may be made of silicon, gallium nitride, or any combination thereof. The insulating portions 107 may be shallow trench isolations (STIs) and may be made of silicon oxide. At least one of the transistors 110 may be made of doped semiconductors.

Figure 2:
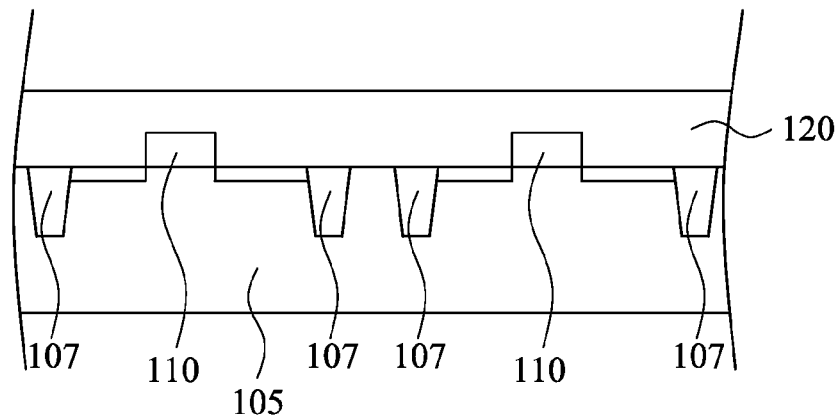

Reference is made to FIG. 2. Subsequently, the manufacturer may form at least one dielectric layer 120 on or above the transistors 110. Taking FIG. 2 as an example, the dielectric layer 120 is formed on the transistors 110. In some embodiments, the dielectric layer 120 may be made of silicon nitride (SiNx), silicon oxide (SiOx), silicon nitride oxide (SiOxNy), or any combination thereof.

Figure 3:
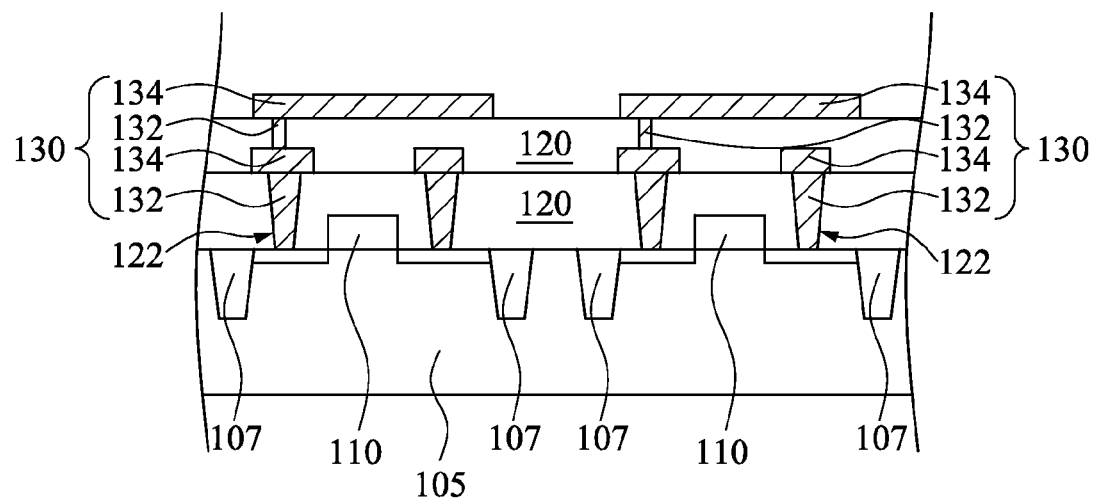

Reference is made to FIG. 3. The manufacturer may form a plurality of connecting structures 130 in the dielectric layer 120. The connecting structures 130 are respectively and electrically connected to the transistors 110. For example, the manufacturer may form at least one via hole 122 in the dielectric layer 120 so that at least a portion of the transistor 110 may be exposed by the via hole 122. Taking FIG. 3 as an example, there are four via holes 122 in the dielectric layer 120 to expose four portions of the transistors 110, respectively. The connecting structures 130, which may include a plurality of plugs 132, are formed in the via holes 122, such that the connecting structures 130 may be electrically connected to the transistors 110, respectively. In some embodiments, the connecting structures 130 may be made of metal, such as titanium (Ti), aluminum (Al), copper (Cu), silver (Ag), or any combination thereof.

In some embodiments, the number of the dielectric layer 120 may be plural so that the dielectric layers 120 may be stacked to each other, and the connecting structures 130 may further include a plurality of wires 134. A portion of the wires 134 may be formed between adjacent two of the dielectric layers 120, and another portion of the wires 134 may be exposed by the dielectric layers 120. The two portions of the wires 134 are separated by one of the dielectric layers 120 and are electrically connected to each other through the plugs 132 of the connecting structure 130. It should be noted that although there are two dielectric layers 120 in FIG. 3, the claimed scope should not limit to this respect. A person having ordinary skill in the art may design a proper number for the dielectric layer 120 according to actual requirements. In some embodiments, if the wires 134 of the connecting structure 130 are not formed, there may be one dielectric layer 120 formed on or above the transistors 110.

Figure 4:
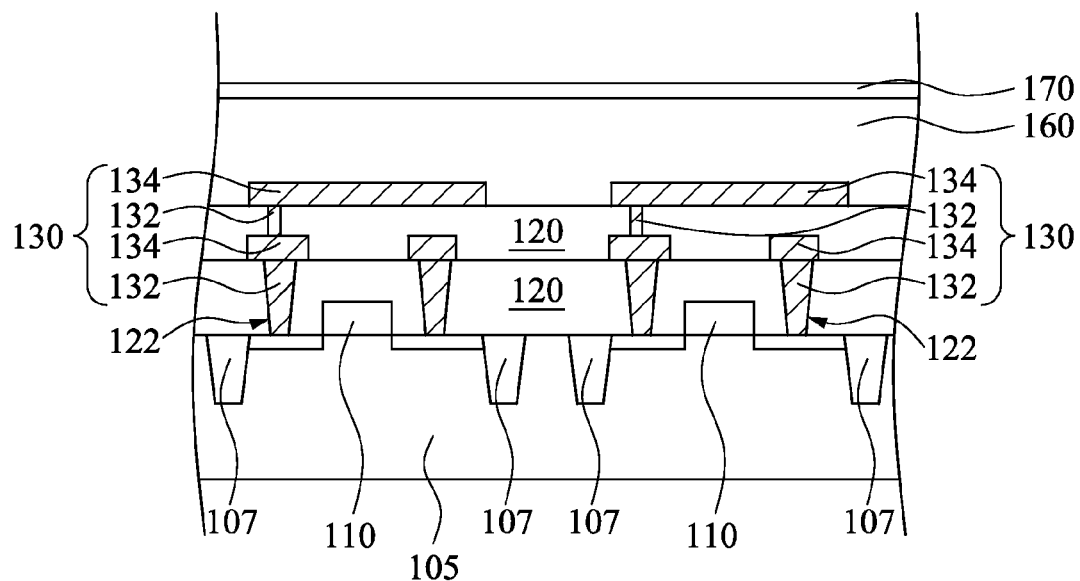

Reference is made to FIG. 4. Subsequently, the manufacturer may form a plurality of separated conductive wells respectively in electrical contact with the connecting structures 130. In greater detail, the manufacturer may form a passivation layer 160 on the connecting structure 130. For example, the manufacturer may form the passivation layer 160 on the wires 134. In some embodiments, the passivation layer 160 may be made of silicon nitride ($SiN_x$), silicon oxide ($SiO_2$), silicon oxynitride ($SiO_xN_y$), or any combination thereof. In some embodiments, the manufacturer may form at least one anti-reflective coating (ARC) layer 170 on or above the passivation layer 160. The anti-reflective coating layer 170 may be made of silicon nitride ($SiN_x$), silicon oxynitride ($SiON_x$), or combinations thereof.

Figure 5:
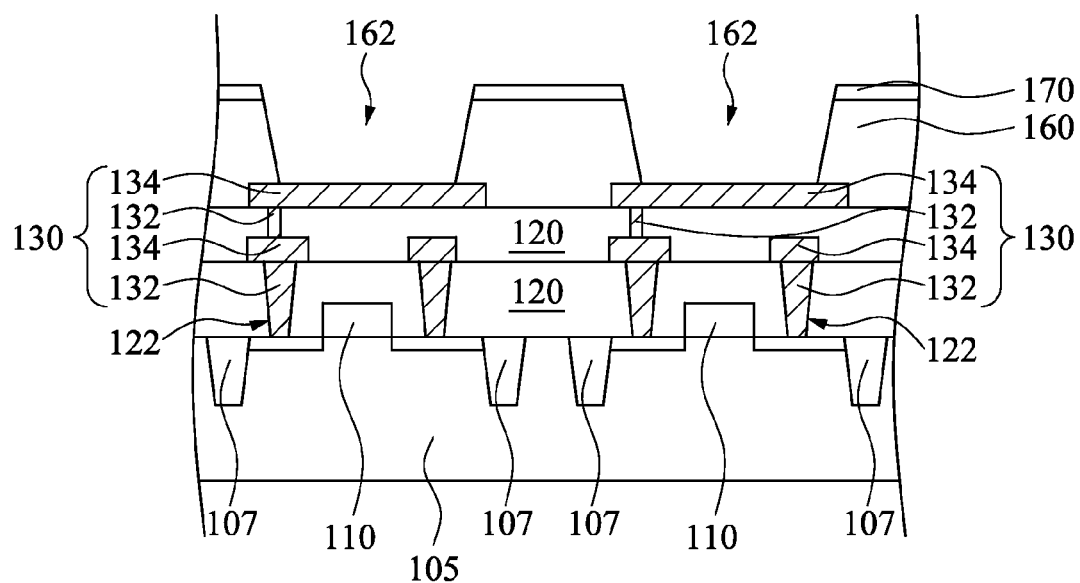

Reference is made to FIG. 5. The manufacturer may form a plurality of through holes 162 in the passivation layer 160. For example, in some embodiments, the manufacturer may form a mask layer on the anti-reflective coating layer 170 and then pattern the mask layer. Then, the manufacturer may sequentially pattern the anti-reflective coating layer 170 and the passivation layer 160 through the patterned mask layer to form the through holes 162 in the passivation layer 160. In some embodiments, the through holes 162 may respectively expose the wires 134. However, if the wires 134 are not formed on the dielectric layers 120, i.e. the passivation layer 160 is formed on the plugs 132 of the connecting structure 130, the through holes 162 of the passivation layer 160 may expose the plugs 132 instead.

Figure 6:
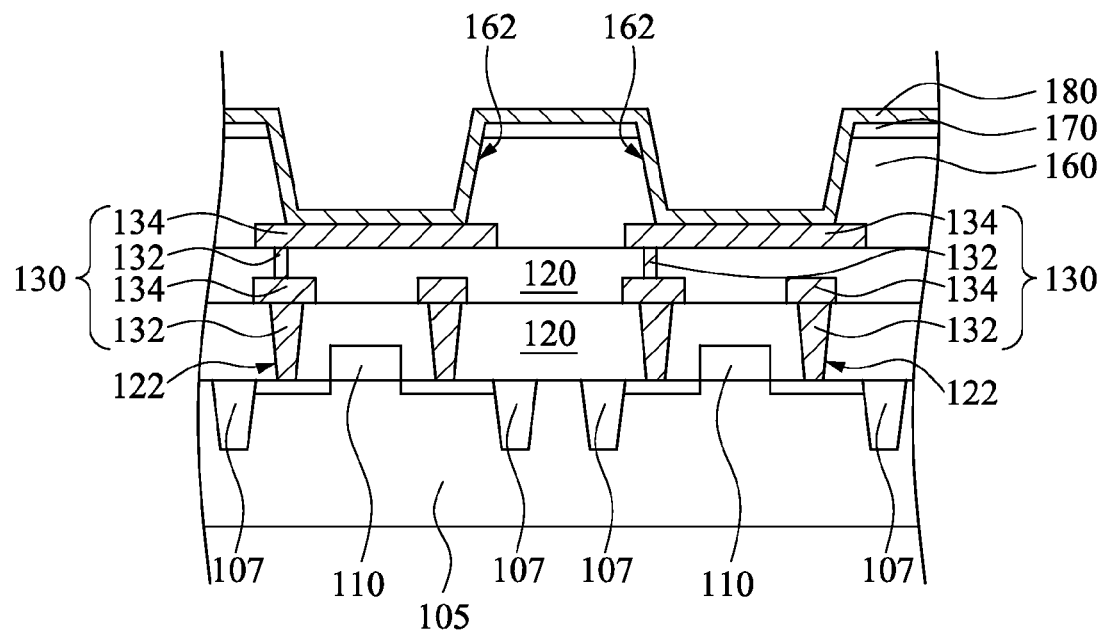

Reference is made to FIG. 6. The manufacturer may conformally form a conductive layer 180 at least covering the passivation layer 160. In some embodiments, the conductive layer 180 covers the anti-reflective coating layer 170, the passivation layer 160, and the wires 134 exposed by the through holes 162. As such, the conductive layer 180 may be electrically connected to the connecting structure 130. In some embodiments, the conductive layer 180 may be made of high conductivity materials, such as titanium (Ti), titanium nitride (TiN), titanium tungsten (TiW), tantalum (Ta), tantalum tungsten (TaN), or any combination thereof.

Figure 7:
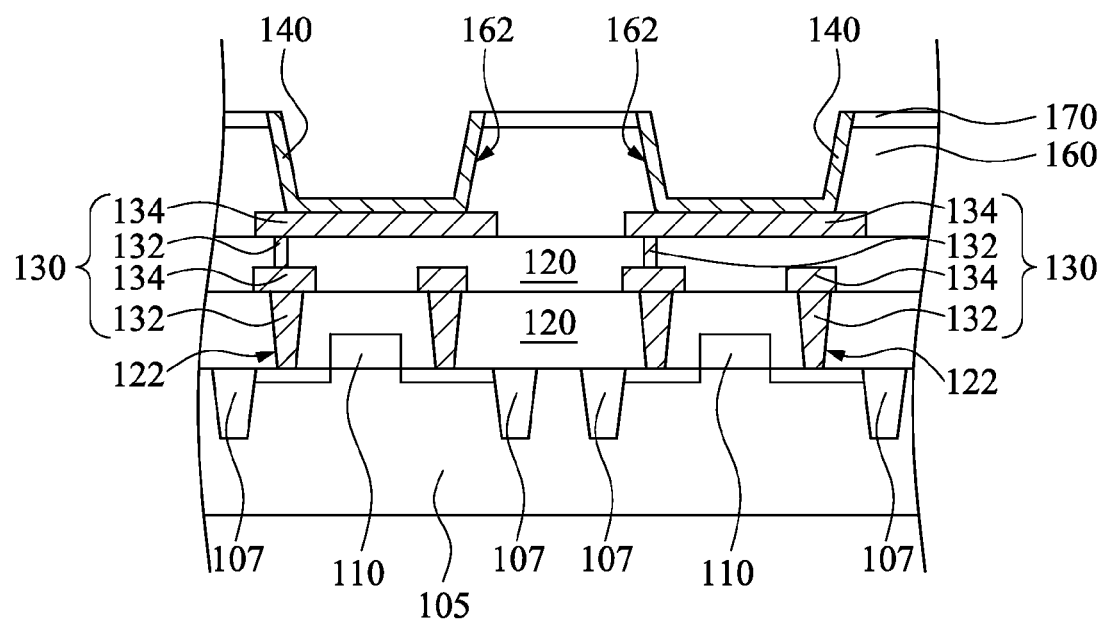

Reference is made of FIG. 7. Subsequently, the manufacturer may remove at least a portion of the conductive layer 180 (see FIG. 6) outside the through holes 162 to form the conductive wells 140 in the through holes 162 of the passivation layer 160. For example, the manufacturer may remove the portion of the conductive layer 180 outside the through holes 162 by chemical mechanical planarization (CMP). In addition, if the anti-reflective coating layer 170 is formed on the passivation layer 160, the anti-reflective coating layer 170 may be a CMP stop layer which is used to control the polishing depth during the CMP process. In some embodiments, since the portion of the conductive layer 180 outside the through holes 162 may be removed by the CMP technique, an additional lithography and etching process may be unnecessary. After the process of FIG. 7, the manufacturing of the sensing integrated circuit is completed.

Structurally, the sensing integrated circuit of FIG. 7 includes a plurality of the transistors 110, at least one of the dielectric layer 120, a plurality of the connecting structures 130, and a plurality of the separated conductive wells 140. The dielectric layer 120 is disposed on or above the transistors 110. The connecting structures 130 are disposed in the dielectric layer 120. The connecting structures 130 are respectively and electrically connected to the transistors 110. The conductive wells 140 are respectively in electrical contact with the connecting structures 130. In some embodiments, the conductive wells 140 of the sensing integrated circuit may be arranged as a two-dimensional array. However, the claimed scope of the disclosure should not be limited in this respect.

In operation, the sensing integrated circuit of FIG. 7 may be disposed in a liquid solution with deoxyribonucleic acid (DNA) molecules. Some of the DNA molecules may move into the conductive wells 140 of the sensing integrated circuit so that the hydrogen ions of the DNA molecules may affect the electrical characteristic of the transistors 110 through the conductive wells 140. Therefore, the information of the DNA molecules may be sensed. In addition, since the conductive wells 140 are separated from each other, crosstalk between adjacent two of the conductive wells 140 may be avoided. Furthermore, in some embodiments, the information of the DNA molecules in the conductive wells 140 may be further transmitted to other devices through the wires 134 of the connecting structures 130. However, the claimed scope of the disclosure should not be limited in this respect.

Figure 8:
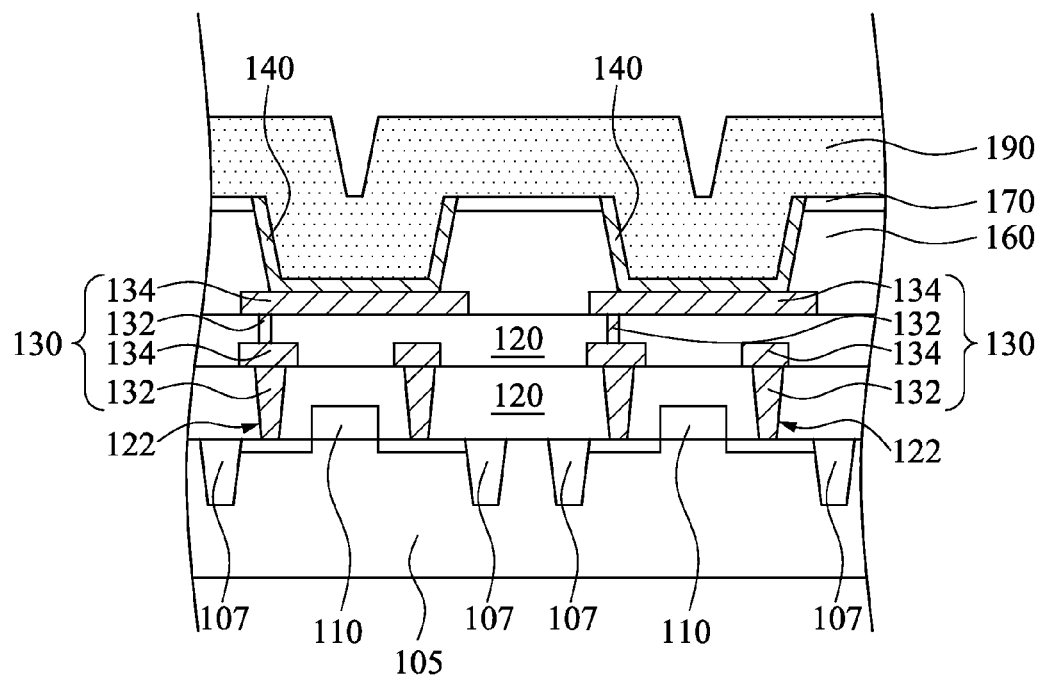
FIG. 8 to FIG. 9 are cross-sectional views of a method for manufacturing a sensing integrated circuit according to various embodiments of the present disclosure.

In some embodiments, the manufacturer may further form a plurality of light sensing films respectively in the conductive wells 140 to form a light sensing integrated circuit. Reference is made to FIG. 8. In greater detail, the manufacturer may firstly form a light sensing layer 190 covering the conductive wells 140. In some embodiments, the light sensing layer 190 may be made of photoconductive materials, such as lead sulfide (PbS), polyvinlcarbazole, selenium (Se), or any combination thereof. The photoconductive materials may become more electrically conductive due to the absorption of electromagnetic radiation such as visible light, ultraviolet light, infrared light, or gamma radiation. For example, PbS is more sensitive to infrared light range.

Figure 9:
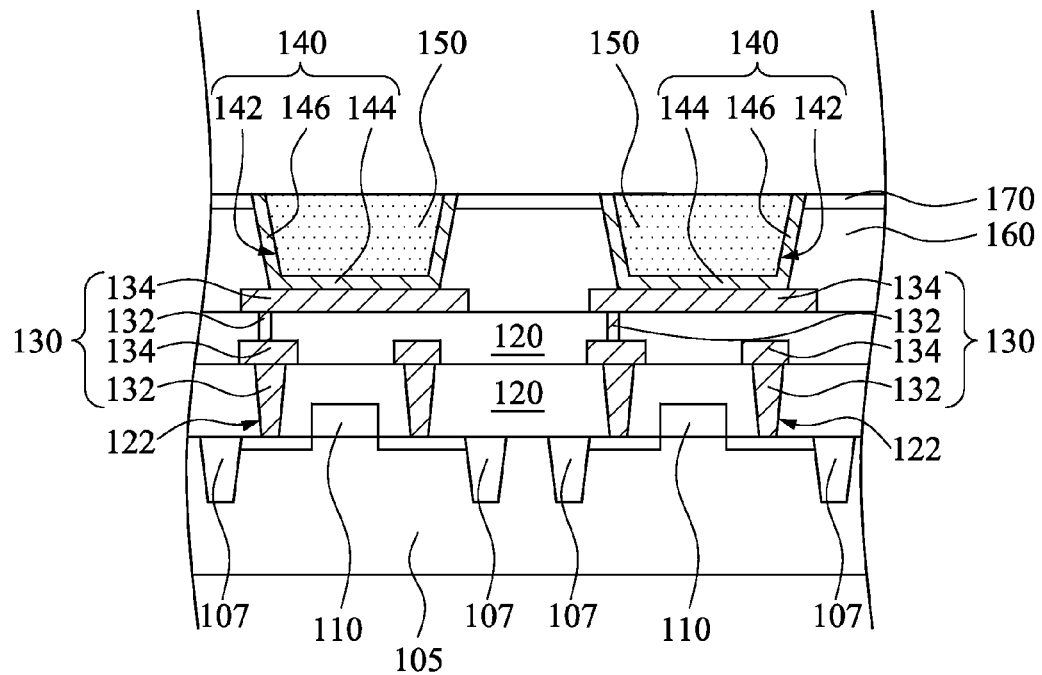

Reference is made to FIG. 9. Subsequently, the manufacturer may remove at least a portion of the light sensing layer 190 (see FIG. 8) outside the conductive wells 140 to form the light sensing films 150 in the conductive wells 140. Therefore, the light sensing films 150 may be separated from each other. In some embodiments, the portion of the light sensing layer 190 may be removed by chemical mechanical planarization (CMP) or photolithography and etching processes. It may be noted that if the portion of the light sensing layer 190 is removed using the CMP technique, other mask layers which may be disposed on the light sensing layer 190 for lithography and etching process may be omitted. After the process of FIG. 9, the manufacturing of the light sensing integrated circuit is completed.

Structurally, the light sensing integrated circuit of FIG. 9 includes a plurality of the transistors 110, at least one of the dielectric layer 120, a plurality of the connecting structures 130, a plurality of the conductive wells 140, and a plurality of the light sensing films 150. The dielectric layer 120 is disposed on or above the transistors 110. The connecting structures 130 are respectively and electrically connecting the conductive wells 140 to the transistors 110. The conductive wells 140 are disposed on or above the dielectric layer 120. The light sensing films 150 are respectively disposed in the conductive wells 140 and thus separated from each other. In some embodiments, the conductive wells 140 of the sensing integrated circuit may be arranged as a two-dimensional array. However, the scope of the claimed disclosure should not be limited in this respect.

In some embodiments, at least one of the light sensing films 150 is made of photoconductive materials such as PbS, polyvinylcarbazole, Se, or any combination thereof. When light is absorbed by the photoconductive materials, the number of free electrons and electron holes increases and raises its electrical conductivity. The transistors 110 may sense the electrical conductivity of the light sensing films 150 through the conductive wells 140 and the connecting structures 130. As such, the light absorbed by the light sensing films 150 may be sensed.

In some embodiments, at least one of the conductive wells 140 is made of high conductivity materials such as Ti, TiN, TiW, Ta, TaN, or any combination thereof. In greater detail, the high conductivity of the conductive wells 140 provides higher sensibility and higher transmission speed of light sensing integrated circuit. As such, the sensibility and the transmission speed may be both improved although the size of the light sensing integrated circuit is shrunk.

In some embodiments, at least one of the conductive wells 140 defines a containing space 142 therein. At least one of the light sensing films 150 is disposed in the containing space 142, and the containing space 142 gets narrower towards the dielectric layer 120. In other words, the containing space 142 gets wider away from the dielectric layer 120. With this configuration, the light absorption areas of the light sensing films 150 may be increased while adjacent two of the conductive wells 140 remain separated from each other.

In some embodiments, the conductive well 140 includes a bottom portion 144 and at least one side wall 146 surrounding the containing space 142. The bottom portion 144 may be disposed on the connecting structure 130 so that the bottom portion 144 is electrically connected to the connecting structure 130. The side wall 146 is connected to the edge of the bottom portion 144. Since the light sensing films 150 are disposed in the containing spaces 142, respectively, the electrons and the holes produced from the light sensing films 150 may move to the bottom portion 144 and the side wall 146 and be sensed. In other words, due to a large contact area between the light sensing film 150 and the conductive well 140, the sensitivity of the light sensing integrated circuit of the present disclosure may be enhanced.

In some embodiments, the light sensing integrated circuit may further include at least one passivation layer 160 disposed between adjacent two of the conductive wells 140. In some embodiments, the light sensing integrated circuit may further include at least one anti-reflective coating layer 170 disposed on or above the passivation layer 160. For example, in FIG. 9, the anti-reflective coating layer 170 is disposed on the passivation layer 160. The anti-reflective coating layer 170 may be a CMP stop layer if the conductive wells 140 and/or the light sensing films 150 are performed using CMP technique. In addition, the anti-reflective coating layer 170 may prevent light reflections during the lithography process, such that the light may be avoid to be incident the area which is not desired to be exposed.

It is understood that the embodiments of the light sensing integrated circuit mentioned above is provided as examples and are not intended to be limiting. The light sensing integrated circuit may have different configurations consistent with the spirit of the present disclosure in alternative embodiments depending on design requirements and manufacturing concerns.

According to some embodiments, a method for manufacturing a sensing integrated circuit including forming a plurality of transistors. At least one dielectric layer is formed on or above the transistors. A plurality of connecting structures are formed in the dielectric layer. The connecting structures are respectively and electrically connected to the transistors. A plurality of separated conductive wells are respectively formed in electrical contact with the connecting structures.

According to some embodiments, a method for manufacturing a sensing integrated circuit including forming a first transistor and a second transistor. At least one dielectric layer is formed on or above the first transistor and the second transistor. A first connecting structure and a second connecting structure are formed in the dielectric layer. The first connecting structure is electrically connected to the first transistor and the second connecting structure is electrically connected to the second transistor. A first conductive well and a second conductive well are respectively formed in electrical contact with the first connecting structure and the second connecting structure. The first conductive well is isolated from the second conductive well.

According to some embodiments, a method for manufacturing a sensing integrated circuit including forming a plurality of transistors. At least one dielectric layer is deposited to cover the transistors. A plurality of connecting structures are formed in the dielectric layer. The connecting structures are respectively and electrically connected to the transistors. A passivation layer is formed on the connecting structures. A plurality of separated through holes are patterned in the passivation layer to expose the connecting structure. A conductive layer is formed at least covering the passivation layer and the through holes. At least a portion of the conductive layer outside the through holes is removed.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for manufacturing a sensing integrated circuit comprising:
    forming a plurality of transistors;
    forming at least one dielectric layer on or above the transistors;
    forming a plurality of connecting structures in the dielectric layer, wherein the connecting structures are respectively and electrically connected to the transistors;
    forming a plurality of separated conductive wells respectively in electrical contact with the connecting structures, wherein at least one of the conductive wells defines a recess;
    forming a light sensing layer that covers the recess, wherein the light sensing layer has a first portion in the recess and a second portion external to the recess; and
    removing the second portion of the light sensing layer.

2. The method of claim 1, wherein the light sensing layer is made of lead sulfide (PbS), polyvinylcarbazole, selenium (Se), or combinations thereof.

3. The method of claim 1, wherein the forming of the conductive wells comprises:
    forming a passivation layer on the connecting structures;
    forming a plurality of through holes in the passivation layer;
    conformally forming a conductive layer at least covering the passivation layer and the through holes; and
    removing at least a portion of the conductive layer outside the through holes to form the conductive wells in the through holes of the passivation layer.

4. The method of claim 3, wherein the removing of the portion of the conductive layer outside the through holes are performed by chemical mechanical planarization.

5. The method of claim 1, wherein at least one of the conductive wells is made of titanium (Ti), titanium nitride (TiN), titanium tungsten (TiW), tantalum (Ta), tantalum tungsten (TaN), or combinations thereof.

6. The method of claim 3, further comprising forming an anti-reflective coating layer on the passivation layer.

7. A method for manufacturing a sensing integrated circuit comprising:
  forming a first transistor and a second transistor;
  forming at least one dielectric layer on or above the first transistor and the second transistor;
  forming a first connecting structure and a second connecting structure in the dielectric layer, wherein the first connecting structure is electrically connected to the first transistor and the second connecting structure is electrically connected to the second transistor;
  forming a first conductive well and a second conductive well respectively in electrical contact with the first connecting structure and the second connecting structure, wherein the first conductive well is isolated from the second conductive well, the first conductive well defines a first recess, and the second conductive well defines a second recess;
  forming a light sensing layer that covers the first recess and the second recess, wherein the light sensing layer has a first portion in the first recess, a second portion in the second recess, and a third portion external to the first recess and the second recess; and
  removing the third portion of the light sensing layer.

8. The method of claim 7, wherein the light sensing layer is made of lead sulfide (PbS), polyvinylcarbazole, selenium (Se), or combinations thereof.

9. The method of claim 7, wherein the forming of the first conductive well and the second conductive well comprises:
  forming a passivation layer on the first connecting structure and the second connecting structure;
  forming a plurality of through holes in the passivation layer to expose the first connecting structure and the second connecting structure;
  conformally forming a conductive layer at least covering the passivation layer and the through holes; and
  removing at least a portion of the conductive layer outside the through holes to form the first conductive well and the second conductive well respectively in the through holes of the passivation layer.

10. The method of claim 9, wherein the removing of the portion of the conductive layer outside the through holes is performed by chemical mechanical planarization.

11. The method of claim 7, wherein the first conductive well is made of titanium (Ti), titanium nitride (TiN), titanium tungsten (TiW), tantalum (Ta), tantalum tungsten (TaN), or combinations thereof.

12. The method of claim 9, further comprising forming an anti-reflective coating layer on the passivation layer.

13. A method for manufacturing a sensing integrated circuit comprising:
  forming a plurality of transistors;
  depositing at least one dielectric layer to cover the transistors;
  forming a plurality of connecting structures in the dielectric layer, wherein the connecting structures are respectively and electrically connected to the transistors;
  forming a passivation layer on the connecting structures;
  patterning a plurality of separated through holes in the passivation layer to expose the connecting structures;
  forming a conductive layer at least covering the passivation layer and the through holes, wherein the conductive layer has first portions respectively in the through holes and a second portion external to the through holes; and
  removing the second portion of the conductive layer, wherein the first portions of the conductive layer are separated from each other.

14. The method of claim 13, further comprising:
  filling a plurality of light sensing films respectively in the through holes and respectively on the first portions of the conductive layer.

15. The method of claim 13, wherein the conductive layer is made of titanium (Ti), titanium nitride (TiN), titanium tungsten (TiW), tantalum (Ta), tantalum tungsten (TaN), or combinations thereof.

16. The method of claim 14, wherein at least one of the light sensing films is made of lead sulfide (PbS), polyvinylcarbazole, selenium (Se), or combinations thereof.

17. The method of claim 14, wherein the forming of the light sensing films comprises:
  forming a light sensing layer covering the first portions of the conductive layer, wherein at least one of the first portions of the conductive layer defines a recess; and
  removing a portion of the light sensing layer external to the recess.

18. The method of claim 17, wherein the removing of the portion of the light sensing layer external to the recess is performed by chemical mechanical planarization.

19. The method of claim 13, wherein the removing of the second portion of the conductive layer is performed by chemical mechanical planarization.

20. The method of claim 13, further comprising forming an anti-reflective coating layer on the passivation layer.

* * * * *